United States Patent
Makower

(10) Patent No.: US 6,746,464 B1
(45) Date of Patent: *Jun. 8, 2004

(54) DEVICE, SYSTEM AND METHOD FOR INTERSTITIAL TRANSVASCULAR INTERVENTION

(75) Inventor: Joshua Makower, Los Altos, CA (US)

(73) Assignee: TransVascular, Inc., Menlo Park, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/181,701

(22) Filed: Oct. 28, 1998

Related U.S. Application Data

(62) Division of application No. 08/730,496, filed on Oct. 11, 1996, now Pat. No. 5,830,222.
(60) Provisional application No. 60/005,164, filed on Oct. 13, 1995.

(51) Int. Cl.[7] .............................................. A61B 17/34
(52) U.S. Cl. .................. 606/185; 606/194; 604/100.01; 604/510
(58) Field of Search ..................... 606/11, 159, 108, 606/153–156, 184, 185; 600/16–18, 106, 107; 128/855; 604/164, 174, 95.01, 100.01, 103.01, 116, 117, 261, 506–513, 103.1

(56) References Cited

U.S. PATENT DOCUMENTS

| | | | |
|---|---|---|---|
| 4,578,061 A | * 3/1986 | Lemelson | .............. 604/164 |
| 4,774,949 A | 10/1988 | Fogarty | |
| 4,794,931 A | 1/1989 | Yock | |
| 4,997,431 A | 3/1991 | Isner et al. | |
| 5,054,492 A | 10/1991 | Scribner et al. | |
| 5,106,386 A | 4/1992 | Isner et al. | |
| 5,167,239 A | 12/1992 | Cohen et al. | |

(List continued on next page.)

FOREIGN PATENT DOCUMENTS

| | | |
|---|---|---|
| EP | 553259 | 10/1991 |
| EP | 511499 | 3/1992 |
| NL | 8900632 | 10/1988 |
| WO | 9200113 | 1/1992 |
| WO | 9210142 | 6/1992 |

(List continued on next page.)

OTHER PUBLICATIONS

N. Bom, C.J. Slager, F.C. Van Egmond, C.T. Lancee, P.W. Serruys; Intra–Arterial Ultrasonic Imaging for Recanalization; Oct. 26, 1987; pp 41–45.

Severin P. Schwarzacher, MD; Peter J. Fitzgerald MD, PhD; Jonas A. Metz, MD; Alan C. Yeung, MD; Steve N. Oesterle, MD; Martin Belef, MS; Robert S. Kernoff, RS; Pau G. Yock, MD. Enhancement of spatial orientation of intravascular ultrasound images with side holes in guiding catheters; Jun. 98; pp 1063–1066.

(List continued on next page.)

Primary Examiner—David O. Reip
(74) Attorney, Agent, or Firm—Robert D. Buyan; Stout, Uxa, Buyan & Mullins, LLP

(57) ABSTRACT

Method and apparatus for utilizing the vascular system as a conduit to reach other vascular and extravascular locations within the body. Included are methods for revascularization wherein the extravascular passageways are formed to permit blood flow between vascular locations. Also included are methods for performing transvascular interstitial surgery (TVIS) wherein extravascular passageways are formed from a blood vessel to another vascular or non-vascular intracorporeal location. Also disclosed are devices usable for forming extravascular passageways in accordance with the invention, or for modifying, valving, maintaining or closing such passageways.

21 Claims, 25 Drawing Sheets

U.S. PATENT DOCUMENTS

| | | |
|---|---|---|
| 5,190,528 A | 3/1993 | Fonger et al. |
| 5,193,546 A | 3/1993 | Shaknovich |
| 5,242,397 A | 9/1993 | Barath et al. |
| 5,287,861 A * | 2/1994 | Wilk |
| 5,330,496 A | 7/1994 | Alferness |
| 5,345,940 A | 9/1994 | Seward et al. |
| 5,354,279 A | 10/1994 | Holfing |
| 5,366,490 A | 11/1994 | Edwards et al. |
| 5,373,849 A | 12/1994 | Maroney et al. |
| 5,419,777 A | 5/1995 | Holfing |
| 5,423,878 A | 6/1995 | Franz |
| 5,429,634 A | 7/1995 | Narciso, Jr. |
| 5,462,523 A | 10/1995 | Samson et al. |
| 5,464,395 A | 11/1995 | Faxon et al. |
| 5,499,630 A | 3/1996 | Hiki et al. |
| 5,507,724 A | 4/1996 | Hoffman et al. |
| 5,538,504 A | 7/1996 | Linden et al. |
| 5,551,954 A | 9/1996 | Buscemi et al. |
| 5,554,182 A | 9/1996 | Dinh et al. |
| 5,570,693 A | 11/1996 | Jang et al. |
| 5,571,086 A | 11/1996 | Kaplan et al. |
| 5,571,151 A | 11/1996 | Gregory |
| 5,588,960 A | 12/1996 | Edwards et al. |
| 5,597,378 A | 1/1997 | Jervis |
| 5,599,300 A | 2/1997 | Weaver et al. |
| 5,614,204 A | 3/1997 | Cochrum |
| 5,628,784 A | 5/1997 | Strecker |
| 5,661,133 A | 8/1997 | Leiden et al. |
| 5,662,609 A | 9/1997 | Slepian |
| 5,665,077 A | 9/1997 | Rosen et al. |
| 5,693,029 A | 12/1997 | Leonhardt |
| 5,704,361 A | 1/1998 | Seward et al. |
| 5,704,926 A | 1/1998 | Sutton |
| 5,713,363 A | 2/1998 | Seward et al. |
| 5,713,853 A | 2/1998 | Clark et al. |
| 5,724,975 A | 3/1998 | Negus et al. |
| 5,724,977 A | 3/1998 | Yock et al. |
| 5,728,123 A | 3/1998 | Lemelson et al. |
| 5,735,847 A | 4/1998 | Gough et al. |
| 5,738,658 A | 4/1998 | Maus et al. |
| 5,771,895 A | 6/1998 | Slager |
| 5,772,629 A | 6/1998 | Kaplan |
| 5,772,632 A | 6/1998 | Forman |
| 5,807,306 A | 9/1998 | Shapland et al. |

FOREIGN PATENT DOCUMENTS

| | | |
|---|---|---|
| WO | 9211890 | 7/1992 |
| WO | 9211895 | 7/1992 |
| WO | 9325263 | 12/1993 |
| WO | 9408653 | 4/1994 |
| WO | 9426341 | 11/1994 |
| WO | 9524235 | 9/1995 |
| WO | 9635464 | 11/1996 |
| WO | 9635469 | 11/1996 |
| WO | 9717029 | 5/1997 |
| WO | 9819614 | 5/1998 |
| WO | 9819618 | 5/1998 |
| WO | 9838939 | 9/1998 |

OTHER PUBLICATIONS

K. Sudhir, P.J. Fitzgerald, J.S. MacGregor, T DeMarco, T.A. Ports, K Chatterjee, P.G. Yock; Transvenous Coronary Ultrasound Imaging; Jul. 91; pp 1957–1961.

K.L. March; Methods of local gene delivery to vascular tissues; 1996; pp 215–223.

J Folkman; Angiogenic Therapy of the Human Heart; 1998; 628–629.

P.G. Yock, D.T. Linker, B.A.J. Angelsen, Dr Tech; Two-Dimensional Intravascular Ultrasound: Technical Development and Initial Clinical Experience; Aug. 1989; 296–304.

Y. Kobayashi, P.G. Yock, P.J. Fitzgerald; perivascular IVUS Landmarks; 1998; pp 35–42.

* cited by examiner

DEVICE, SYSTEM AND METHOD FOR INTERSTITIAL TRANSVASCULAR INTERVENTION

This is a division of U.S. patent application Ser. No. 08/730,496, filed Oct. 11, 1996, now U.S. Pat. No. 5,830,222, with a claim of priority to U.S. Provisional Patent Application Serial No. 60/005,164 filed on Oct. 13, 1995.

BACKGROUND OF THE INVENTION

Percutaneous Transvascular Arterial Bypass

Atherosclerosis is a progressive disease process in which the flow within the lumen of an artery becomes restricted by a blockage, typically referred to as an athersclerotic plaque. In the heart, as well as the periphery, a blockage of an artery can result in pain, disfunction and even death. Numerous methods have been employed over the years to revascularize the tissue downstream of an arterial blockage. These methods include bypass grafting—using artificial, in-situ venous, or transplanted venous grafts, as well as angioplasty, atherectomy and most recently, laser transmyocardial revascularization. Bypass grafting has been extremely successful; however, the procedure requires extensive surgery. Recently, newer techniques such as the transthoracic endoscopic procedure being pursued by the company, Heartport, Inc. and Cardiothoracic Systems, Inc., illustrate the need for a less invasive method of bypassing coronary vessels. These procedures are very difficult to perform, and may not be widely applicable. While transmyocardial laser revascularization, a technique in which small holes are drilled through the wall of the heart, looks promising, the method of action is not yet well understood, and problems exist with the use of laser energy to create the channels. Yet clinicians are still very interested in the technique because is has the potential to be minimally invasive, and does not require the patient to be placed on cardiopulmonary bypass.

In the 1970s several cardiovascular surgeons experimented with the use of cardiac veins for revascularization. The procedure was for use on patients which had severely diffuse stenotic coronary vessels. The technique involved using an intervening graft from the internal mammary artery or an aortic attachment to a saphenous vein. Instead of sewing the grafts to the distal coronary artery, the grafts were attached to the coronary or cardiac vein in the same location. The proximal portion of the vein was then ligated to prevent a shunt, and the patient was then taken off cardiopulmonary bypass, and chest was closed. In this model, the vein were 'arterialized', allowing flow in a retrograde fashion in a effort to bring oxygenated blood to the venules and capillaries of the heart. The success of this technique varied greatly, and was for the most part abandoned. Problems included stenosis at the anastomosis, intracardiac hemorrhages from ruptured venules, and thrombosis of the grafts.

The devices, systems and methods proposed in this disclosure suggest a new method of percutaneous revascularization. Here, the cardiac veins may either be arterialized, or may be simply used as bypass grafts. There is no literature to suggest that this has been ever been attempted. While in-situ bypass grafts have been made in the periphery, still an incision is made to attach and ligate the vein ends. Another procedure which bears some resemblance to this technique is called the TIPS procedure—transjugular intrahepatic portosystemic shunt. In this procedure a stent is advanced into liver tissue to connect the portal vein to the inferior vena cava. While this procedure can be accomplished percutaneously, it is not for the purpose of revascularization of an organ or to bypass a blockage within a vessel, does not permit retrograde flow within either of the two vessels, is not performed with an accompanying embolization, and requires the use of a stent. Further, the devices and methods used in that setting are too large and do not have the directional capability necessary for use in smaller vessels such as those found in the heart.

Transvascular Intervascular Interstitial Surgery

Open surgery was for many years the only way to gain access to tissues to perform a surgical maneuver. With the advent of optics, various endoscopic procedures were developed. Initially, these procedures utilized natural orifices such as the urinary tract, oral cavity, nasal canal and anus. Most recently, new techniques using transabdominal and transthoracic ports have been developed. These thorascopic or laparoscopic procedures essentially use instruments which are long-shafted versions of their counterparts in open surgery. General anesthesia is usually required, and there are still several smaller wounds which require healing.

Another problem that exists with this approach is the identification of anatomically consistent reference points. For precise surgery, such as in the brain, a frame is usually attached to the patients head to provide this reference. More recently, a 'frameless' system has been developed which utilizes a much smaller frame mounted with several light emitting diodes (LEDs). The LEDs are correlated to LEDs on the instrument itself using three cameras mounted to the ceiling. This aid in the correlation of the frame to the landmarks, and assures proper positioning of the instrument. While this seems like an extensive effort, it underlines the importance of gaining access to the exact location desired.

Traditionally, the vascular system has been entered for the sole purpose of addressing a vascular problem. Angioplasty, atherectomy, stents, laser angioplasty, thrombolysis and even intracardiac biopsy devices have all been designed for intravascular use.

SUMMARY OF THE INVENTION

A device, system and method are provided for utilizing the vascular system as a conduit through which an intervention can be rendered within and beyond the vascular wall. In accordance with one embodiment, a device is introduced into the vascular system at a convenient entry point and is advanced to a particular target location at which point an opening is created to allow the passage of the device or another a device or devices through or around the port into the space beyond the interior of the vessel. In one embodiment, a system is used to act as an access port to the space through which a procedure may be performed. Such a procedure may be used worthwhile for cooling or ablating a volume of tissue, injecting or infusing a drug, substance or material, cutting, manipulating or retrieving tissue, providing access for endoscopic visualization or diagnosis, the placement of an implantable or temporary device, creating an alternative tract through which blood may be conducted for the purpose of revascularization or for performing some other surgical procedure. In another embodiment, the system is used to achieve an opening in an adjacent vessel proximate to the first opening to allow the passage of blood through the channel created by the device. Such a procedure may be useful for creating alternative vascular channels to provide alternative revascularization routes, such as in the heart between the coronary arteries and cardiac veins. With further specificity, such a system may be used to bypass coronary arteries and provide for cardiac venous arterialization, or segmental grafting. In addition, the stability of vascular supply orientation to anatomic landmarks provides a simple method of repeatedly accessing perivascular structures under imaging or other guidance. This may be particularly useful for accessing areas within the brain, kidney, lung, liver, spleen as well in other tissues, and represents a significant advantage over tissue marking localization, external frames or so-called "frameless" external instrument orientation systems. In a final embodiment, the system is used to create an opening in the vessel proximally, tunneling through the tissue adjacent to the vessel, and re-entering the vessel at a distal point. This may be useful for providing an alternate path for blood flow around a lesion with a vessel.

BRIEF DESCRIPTION OF THE DRAWINGS

FIG. 24b is a side view of the locking or anchorable guidewire of FIG. 24a.

DETAILED DESCRIPTION OF THE PREFERRED EMBODIMENTS

The invention herein utilizes the vascular system as a perfect conduit to any region of the body. The devices, systems and methods described here provide a new way that the interstitial space can be accessed for surgical purposes. The invention described herein provides a system for gaining percutaneous access to any part of the body through the vascular system, and provides the basic set of instrumentation for accomplishing several surgical and medical endpoints.

The present invention provides a percutaneous means for revascularizing an organ fed by a diseased vessel. In accordance with further embodiments of the present invention, a complete multiple coronary artery bypass may be accomplished without cracking open the chest, general anesthesia or cardiopulmonary bypass.

In order to provide an overall understanding of the present invention, the method of the invention will be discussed with reference to the device's use to bypass a lesion within the coronary artery in the heart percutaneously. However, it will be understood by persons of ordinary skill in the art that the general method, system and device as described herein are equally applicable to the surgical manipulation of any perivascular structures. This invention represents a new concept in minimally invasive surgery which is that the vascular system may be used purely as a conduit to a desired surgical point. Under the proper guidance, at that surgical point, the perivascular space can be penetrated by a device so as to allow for the insertion of various instrumentation to effect a surgical effect. Some examples of these procedures may include but are not limited to: transvascular intracranial access and subsequent therapeutic or diagnostic intervention to various perivascular tumors, hemorrhages, stroke-effected areas and diseased zones; transvascular tissue biopsies from the brain, heart, kidney, liver, lung or bone; tralsvascular implantation of drugs, materials or devices such as sensors, radioactive seeds, ferromagnetic particles, balloons, cells or genetic material.

Figure 1:
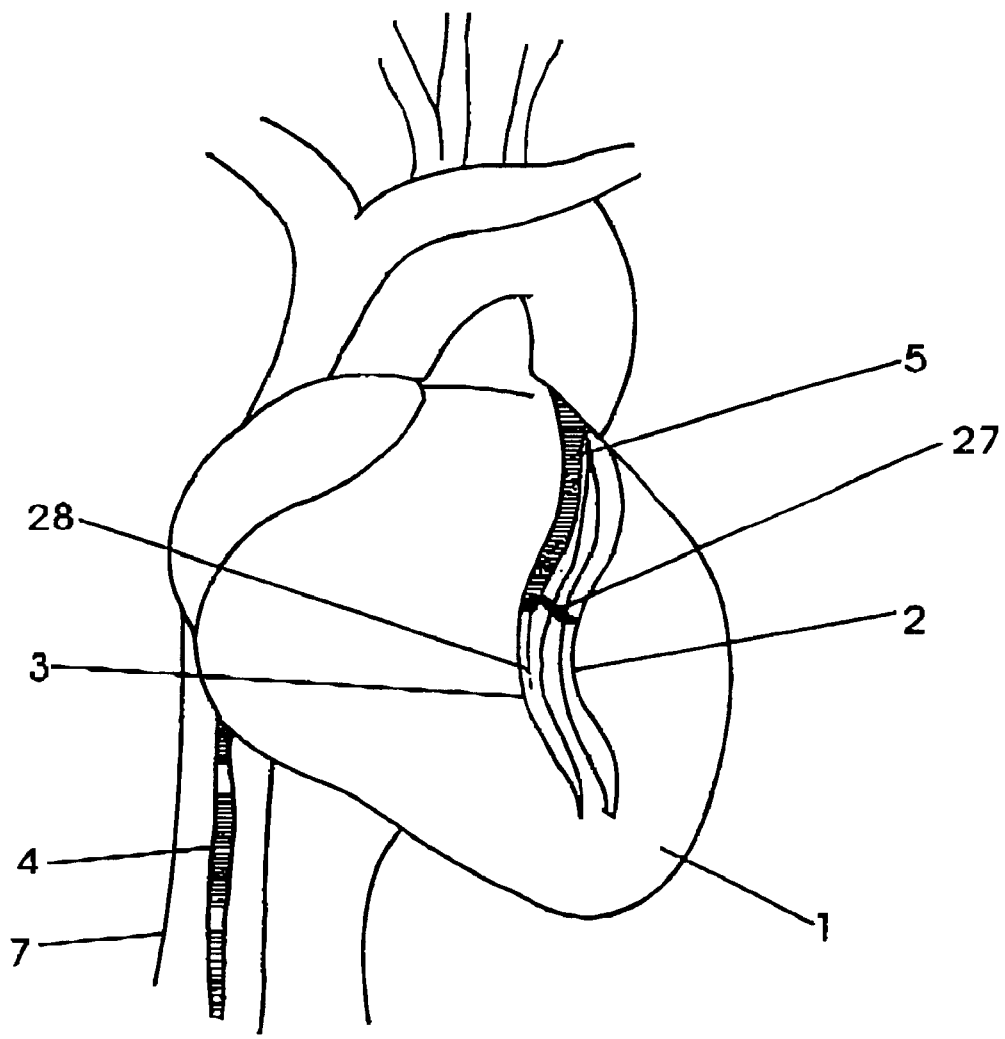
FIG. 1 is a schematic showing of a human heart wherein a blood flow channel has been formed between a coronary artery and a coronary vein in accordance with one embodiment of the present invention.

Referring to FIG. 1, a typical coronary sinus guide catheter 4 is shown having been advanced up the vena cava 7 and into the heart 1. Although not shown, the guide catheter 4 has been advanced into the coronary sinus within the right atrium of the heart 1. This guide catheter will be of the type generally known in the art to include a tip of sufficient compliance and size to assure atraumatic insertion into the coronary sinus, with a balloon at its distal end to permit the retrograde injection of contrast to permit imaging of the cardiac venous system. The transvascular interstitial surgery (TVIS) guide catheter 5 is inserted through the guide catheter and advanced through one cardiac vein 3 over a guide wire 28 to a desired point adjacent to a coronary artery 2. The figure shows a TVIS probe 27 being advanced through the TVIS guide catheter 5 through an opening in the cardiac vein 3 to a desired point in the coronary artery 2.

Figure 2:
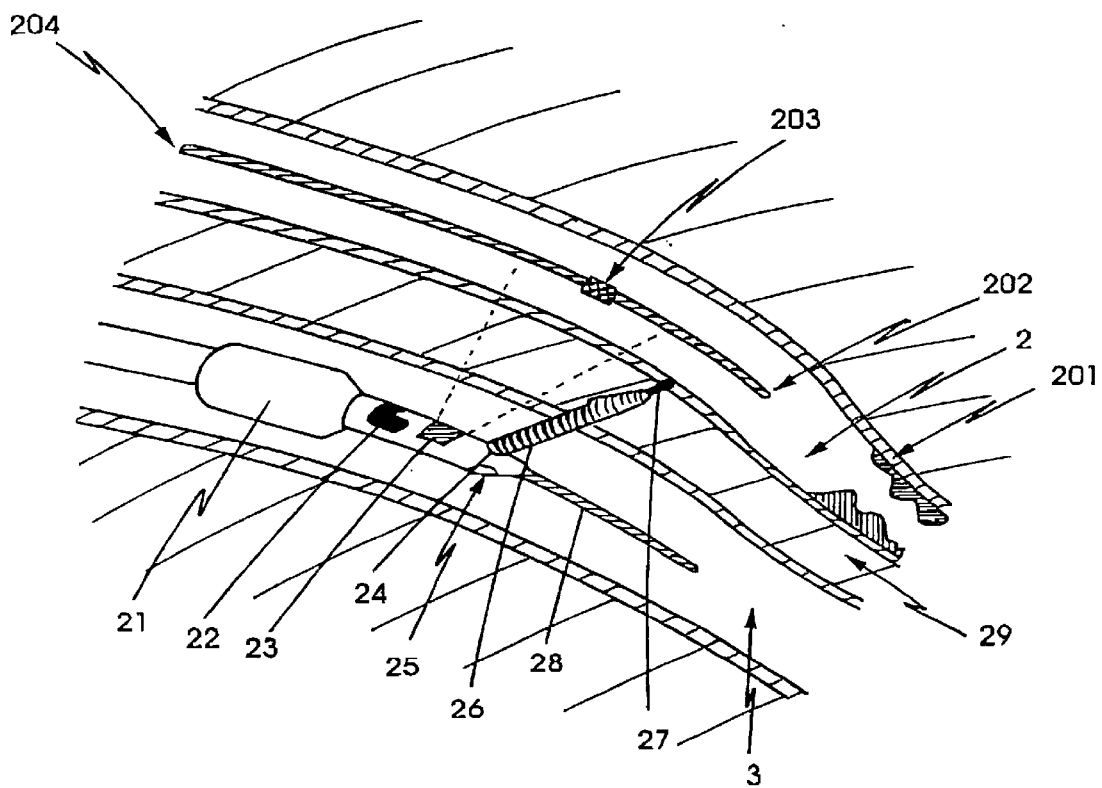
FIG. 2 is a sectional view through two adjacent blood vessel with a tissue penetrating catheter device of the present invention positioned in one of the blood vessels and being used to form a penetration into the adjacent blood vessel.

FIG. 2 shows in more detail the various functions and components which could be included on the TVIS guide catheter 5. Here the TVIS guide catheter 5 is shown within a cardiac vein 3 being advanced over guidewire 28. A balloon 21 is provided on TVIS guide catheter 5 for the purpose of blocking flow, stabilizing the catheter within the lumen, or dilating the passageway. TVIS guide catheter 5 is also provided with either or both active orientation detection means 23 and passive orientation detection means 22. Persons of ordinary skill in the art could identify that the passive orientation means 22 may be configured of any of a known set of materials which would allow for the radiographic, fluoroscopic, magnetic or sonographic detection of the position and orientation of the distal portion of the TVIS guide catheter 5 within the body. These materials include but are not limited to any radiopaque material such as barium or steel, any ferromagnetic material such as those with iron, or any material or composite which provides sufficient interference to sound waves such as trapped air bubbles, scored metal or several laminates. The active orientation detection means 23 permits the proper 360 degree orientation of the distal portion on the TVIS guide catheter 5 within the lumen of the vessel, in this case cardiac vein 3. This active orientation means 23 can utilize any one but is not limited to one of the following technological schemes: the active orientation means 23 may be a simple piezo-electric, wire or silicon based slab capable of sending and receiving a signal to detect the presence or velocity of flow within an adjacent vessel; this same device could be an array of receivers in relationship to a transmitter for the purposes of providing an image of the surrounding tissue; this same device could also be a simple transmitter capable of sending a signal to guidewire 202 positioned in this case within the coronary artery 2—where guidewire 202 is further modified to include a small receiver/transmitter 203 and wire bundle 204 capable of returning a signal to the operator upon detection of the signal emitted by active orientation means 23; the reverse system is also applicable where the small receiver/transmitter 203 sends a signal to active orientation means 23; the same could also be said for orientation means 23 to send or receive signals to or from any of a series of known signal generators including sonic, electromagnetic, light or radiation signals. The TVIS guide catheter 5 is provided in this case with an additional opening to allow for the selective injection of contrast or fluid into the vessel, in this case cardiac vein 3. Once the orientation of the TVIS guide catheter 5 is assured, the TVIS probe 27 and TVIS sheath 26 may be advanced through the wall of the cardiac vein 3 into the interstitial space 29 and into the coronary artery 2. The TVIS probe 27 and TVIS sheath 26 do not necessarily need to be advanced simultaneously and may have the following configurations: the TVIS sheath 26 may be a sharp tipped or semi-rigid cannula capable of being inserted into the tissue alone; the TVIS probe 27 may be a relatively rigid wire, antenna, light guide or energy guide capable of being inserted into the tissue alone with the support or TVIS sheath 26; or further the TVIS probe 27 and TVIS sheath 26 may be operatively linked where the two are inserted together into the tissue. The TVIS probe 27 and/or the TVIS sheath 26 provide the initial connection between the two vessels, the cardiac vein 3 and coronary artery 2. Once the TVIS sheath 26 is placed, a more floppy guidewire can be placed through it to permit the advancement of additional instrumentation in the case where another lumen is to be entered. Alternatively, no guidewire may be necessary if the interstitial space is being entered to perform a different type of procedure. This procedure may be used to create a bypass path from coronary artery 2 around a coronary stenosis 201, into the cardiac vein 3 and in some cases, back into the coronary artery 2.

Figure 3:
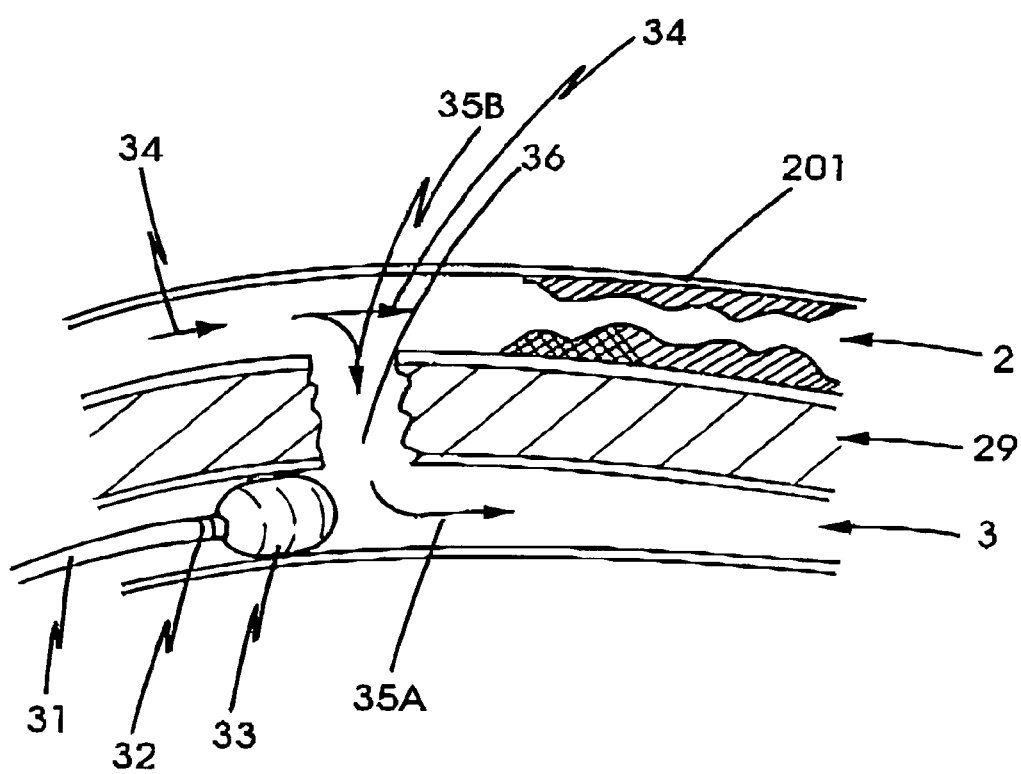
FIG. 3 is a sectional view through an obstructed artery and an adjacent vein, wherein a blood flow channel has been formed between the artery and the vein and an embolization device has been positioned in the vein, proximal to the blood flow channel, to cause arterial blood to flow through the blood flow channel, into the lumen of the vein, and through the lumen of the vein in a directional opposite normal venous flow.
Figure 4:
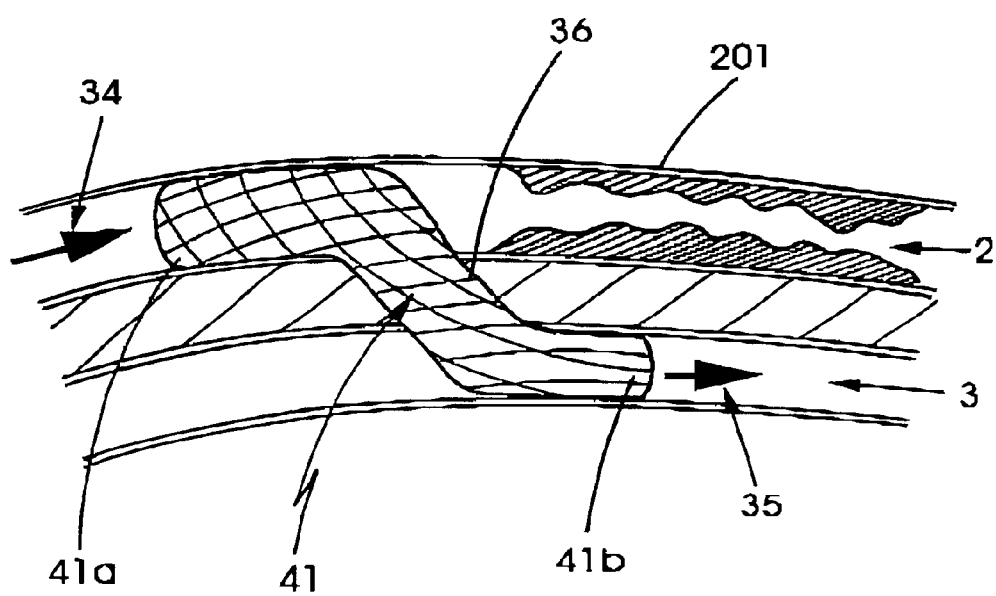
FIG. 4 is a sectional view through an obstructed artery and an adjecent vein, wherein a blood flow channel has been formed between the artery and the vein and a connector apparatus, which may optionally be covered, has been placed within the blood flow channel and protrudes into the lumens of the artery and vein.
Figure 9:
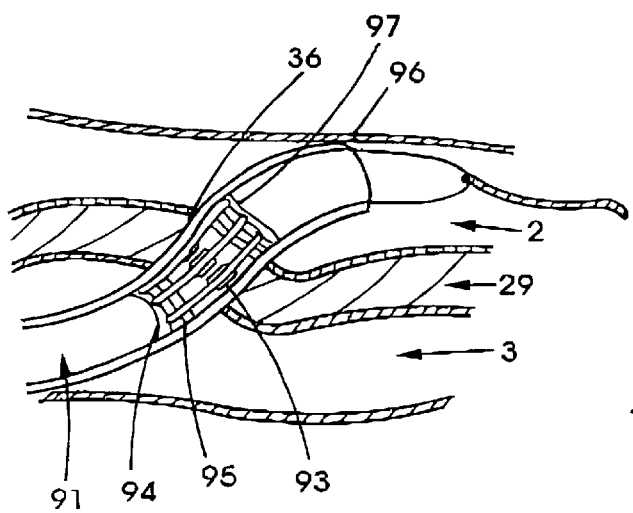
FIGS. 9, 9a-9c are a step-by-step showing of the placement of connector apparatus between openings formed in adjacent blood vessels, in accordance with one embodiment of the present invention.
Figure 12:
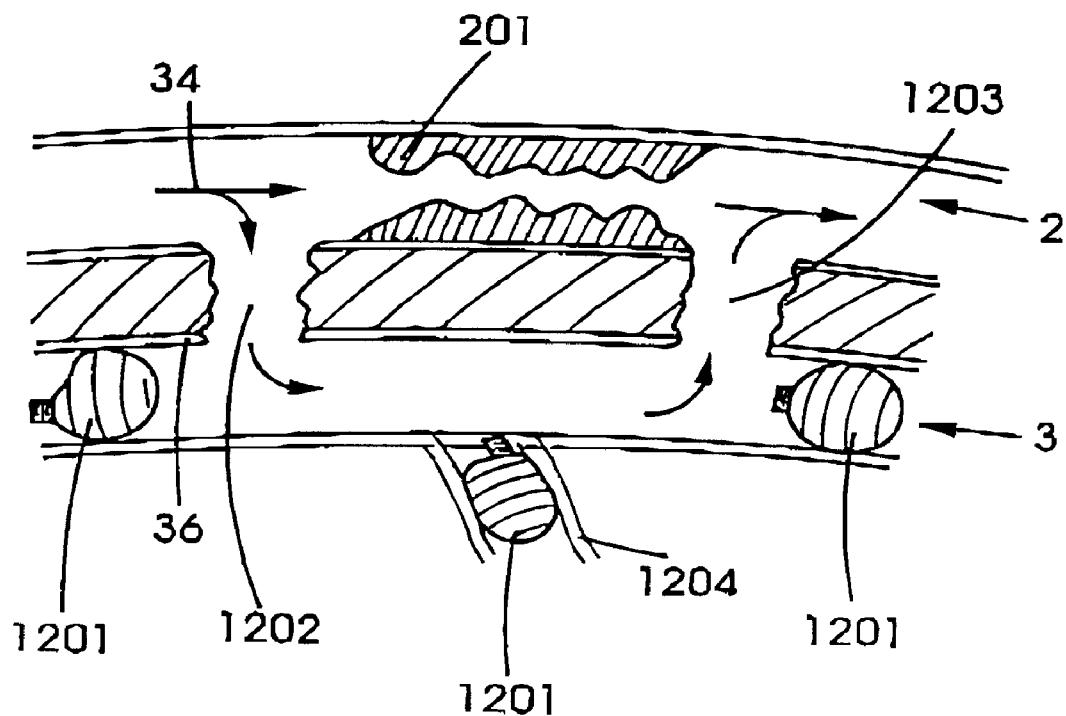
FIG. 12 is a sectional view through an obstructed artery and an adjacent vessel, wherein a percutaneous in-situ bypass procedure has been performed to bypass the obstruction in the artery.

To prevent coronary blood from shunting directly back into the right atrium through the coronary sinus, it is necessary to block flow at one or more points within the cardiac vein. Referring to FIG. 3, once the hole is made, and it is determined that it is of sufficient size, an embolization device, such as an embolization balloon 33, can be used to block flow in the cardiac vein 3 in a region proximal to tissue track 36. This maneuver ensures that coronary arterial flow 34 passes through tissue track 36 and results in a retrograde cardiac venous flow indicated by arrows 35a and 35b. The embolization balloon 33 is placed using embolization catheter 31 and upon proper inflation, is detached via a detachable segment 32. Those skilled in the art will recognize that any one of several devices and materials are available for the purpose of embolization. These include detachable balloons, coils, strands of coagulation producing material, microfibrillar collagen, collagen sponge, cellulose gel or sponge such as Gelfoam (TM), or special stents. FIG. 3 shows how these devices can be used to re-arterialize the venous system distal to the connection. However, as shown in FIG. 12, it is possible to simply provide a bypass path by performing the same procedure in reverse in an appropriate downstream location. It should be mentioned that these embolization devices may also be used to block off any unwanted tributaries branching off from the cardiac vein. FIGS. 4 and 9 are described later in this document.

FIGS. 10A–10B and 11A–11B depict two additional schemes of embolization devices in accordance with the invention which also may have utility to accomplish the desired closure.

Figure 10A:
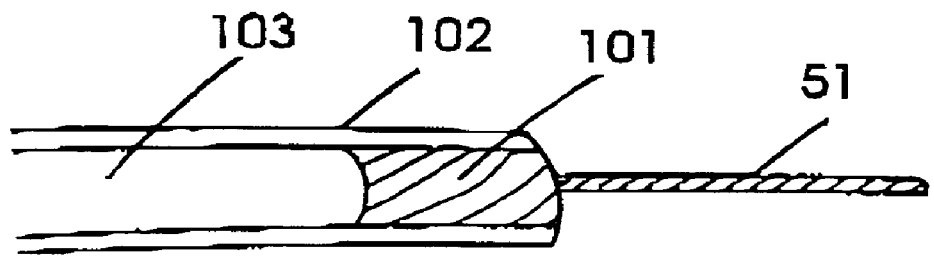
FIG. 10a is a partial side elevational view of a catheter and guidewire wherein a collagen sponge type embolization device is positioned within and deployable from the catheter to embolize the lumen of a blood vessel in accordance with one aspect of the present invention.
Figure 10B:
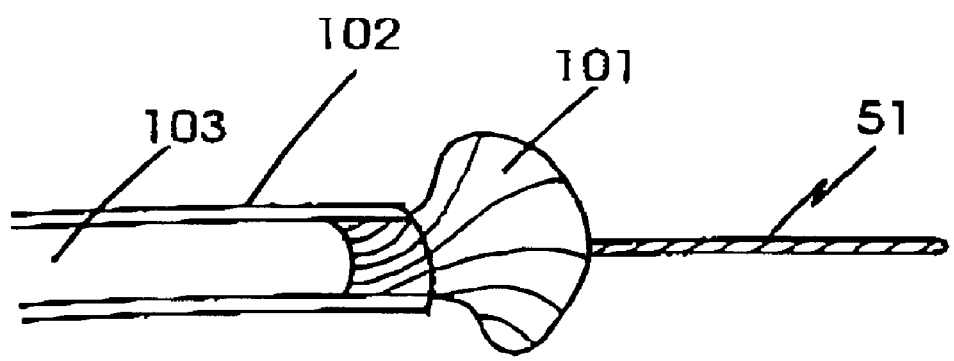
FIG. 10b is a showing of the catheter device and guidewire of FIG. 10a, wherein the collagen sponge type embolzation device has been partially advanced out of the cistal end of the catheter in an over-the-wire fashion.

FIG. 10A depicts a compressed collagen sponge 101 located within an outer sheath 102, capable of being delivered over guidewire 51. Once the guidewire 51 is advanced into vessel which is to be embolized, outer sheath 102 is withdrawn over inner core 103 to permit collagen sponge 101 to expand into the vessel as seen in FIG. 10B. Once completely delivered, the guidewire 51 and the catheter assembly 102 and 103 are withdrawn, leaving the sponge in place.

Figure 11A:
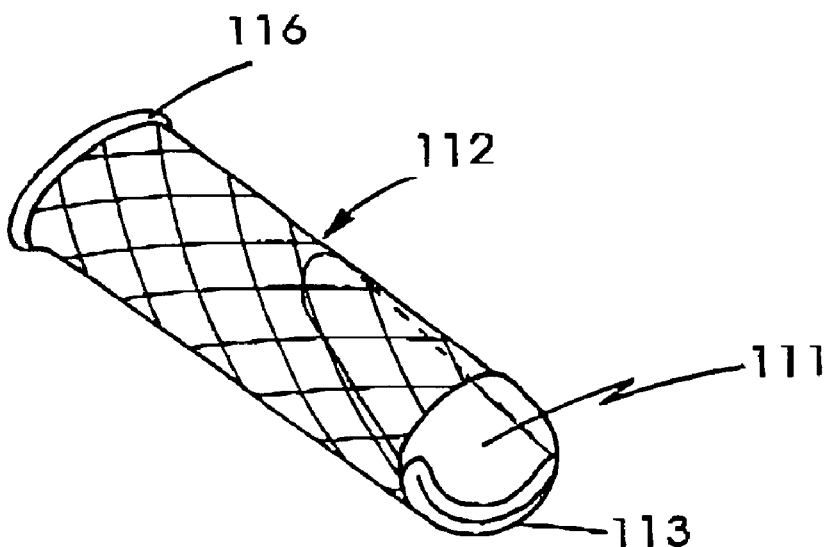
FIG. 11a is a perspective view of an embodiment of a one-way valve stent of the present invention.
Figure 11B:
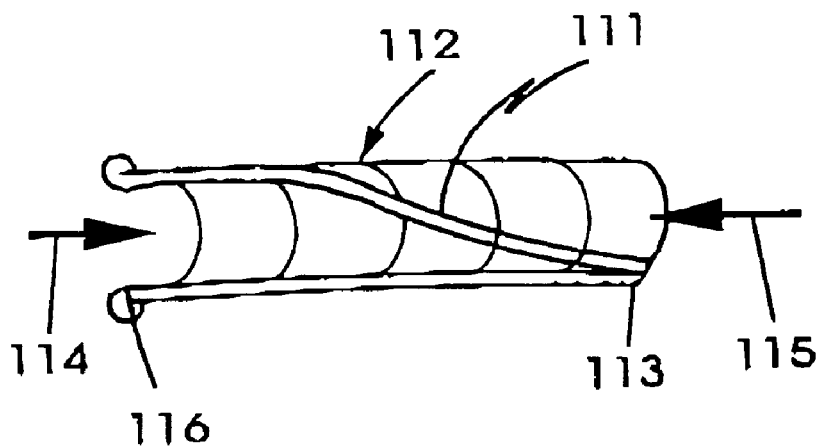
FIG. 11b is a side elevational view of the one-way valve stent of FIG. 11b.

FIG. 11A depicts a one-way valve stent 112. Membrane 111, disposed within the stent 112, is configured to be cylindrical at side 116, yet collapsed upon itself at side 113 to form a one-way valve. As seen in longitudinal section FIG. 11B, this allows flow in the direction of arrow 114 and the advancement of devices in this direction, but prevents flow in the direction of arrow 115 as well as preventing devices from entering from that direction. The one-way valve stent 112 can be easily placed over a catheter into the desired location and expanded to fit in position. Once the internal delivery catheters are removed, membrane 111 is allowed to collapse, instantly creating a value-like action.

In a further embodiment, an embolization device may not be necessary, as shown in FIG. 4. A stent 41 is placed through tissue track 36 such that coronary portion 41a and venous portion 41b are positioned as shown. Stent 41 may be covered by a material, a dense mesh or a matrix of cells, such that coronary flow 34 cannot easily flow through the side wall of stent 41 towards stenosis 201, but instead is rerouted through stent 41 into cardiac vein 3 to produce retrograde cardiac venous flow 35. In this figure, the position of the stent suggests that the TVIS guide catheter had been placed within the coronary artery 2, and the tissue track 36 was created in the arterial to venous direction. This would allow for the proper positioning of a guidewire and subsequently the stent to allow for the device to be oriented in the arterial to venous direction. It should be clear that it is also possible for a similar stent to be placed downstream (in a location, for example, corresponding to region 1203 in FIG. 12 accessed through vein 3) from the venous to arterial direction to permit a complete bypass of the stenosis 201 in the coronary artery 2. Stent 41 must have the capability of being dimensioned such that proximal portion 41a and distal portion 41b may be expanded into shape which closely approximates the respective wall of the vessel into which it is placed. Alternatively, as shown in FIG. 4a, the stent 410 may be placed such that proximal portion 410a and distal portion 410b do not block flow, but simply act to maintain the dimensions of tissue track 36.

Figure 4A:
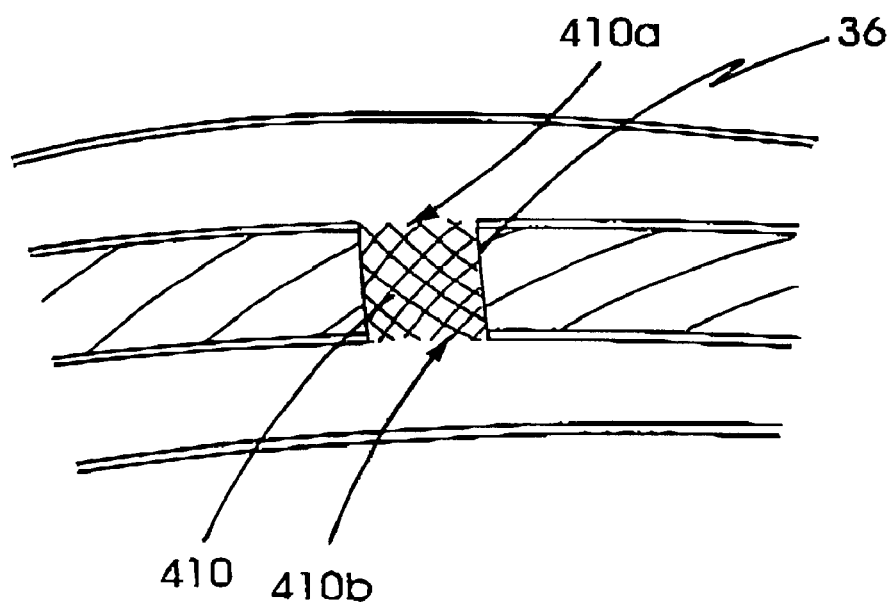
FIG. 4a is a sectional view through an obstructed artery and an adjacent vein, wherein a blood flow channel has been formed between the artery and the vein and a connector apparatus, which may optionally be covered, has been placed within the blood flow channel only.
Figure 5:
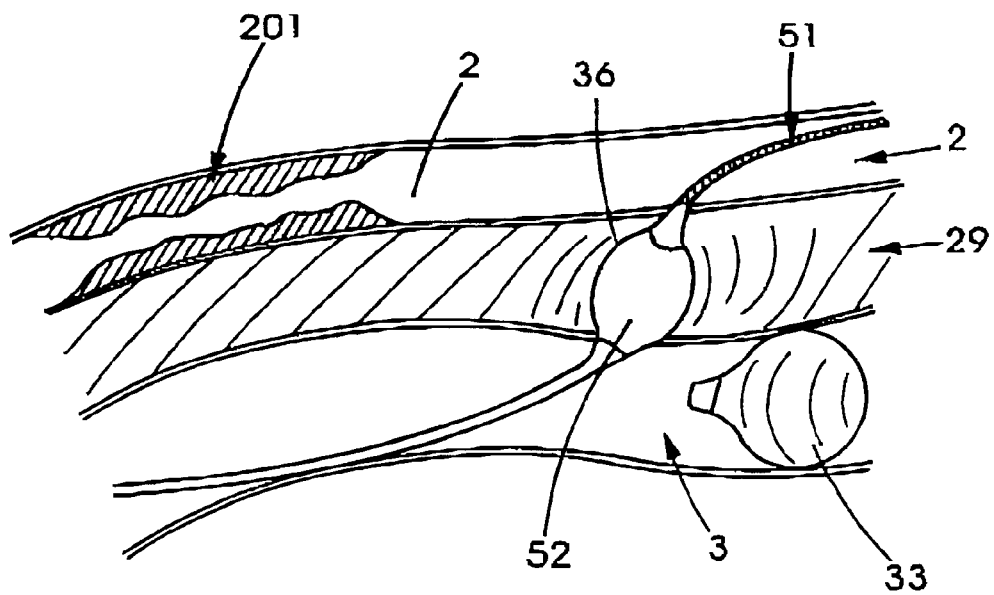
FIG. 5 is a sectional view through an obstructed artery and an adjacent vein, wherein a penetration tract has been formed between the artery and the vein and a dilation apparatus has been introduced into the penetration tract to enlarge the penetration tract to form a blood flow channel.

FIG. 5 shows how tissue track 36 can be dilated by a standard balloon 52 advanced over guidewire 51 for the purpose of ensuring that tissue track 36 is wide enough to receive the flow. Further, this step may be necessary to properly dimension the tissue track 36 prior to insertion of other devices such as the stent 41 seen in FIG. 4, or stent 410 seen in FIG. 4a.

Figure 6:
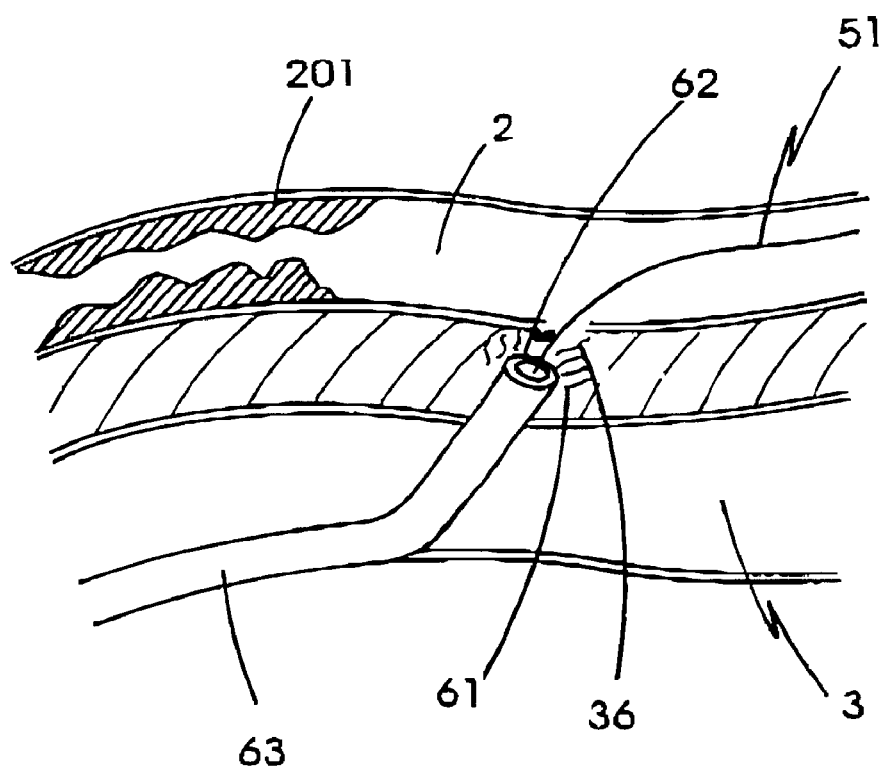
FIG. 6 is a sectional view through an obstructd artery and an adjacent vein, wherein a penetration tract has been formed between the artery and the vein and an energy-emitting channel sizing device has been introduced into the penetration tract to enlarge the penetration tract to form a blood flow channel.

A stent may not be necessary to maintain the size of tissue track 36 if enough material can be removed or ablated between coronary artery 2 and cardiac vein 3. In FIG. 6, a vaporization catheter 63 is shown being advanced over guidewire 51. Here, energy 61 is delivered to the tissue track 36 through the distal portion 62 of the vaporization catheter 63 to create a properly dimensioned connection between artery and vein. Those skilled in the art will recognize that this vaporization catheter 63 may also be used to deliver thermal, cutting, welding or coagulative energy via several means including but not limited to laser, bipolar or monopolar radiofrequency (RF), microwave, ultrasound, hot-wire, or radiation.

Figure 7:
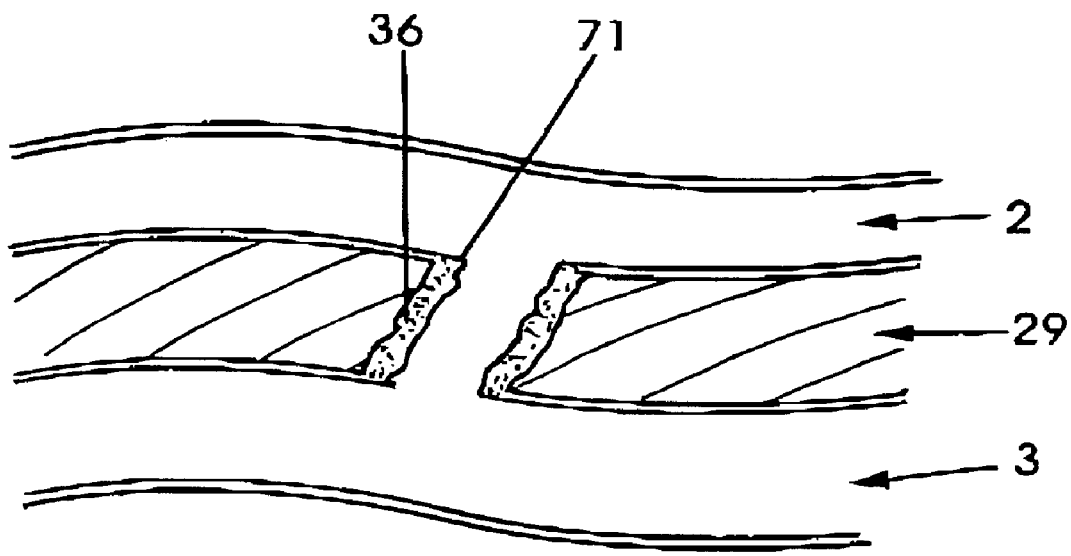
FIG. 7 is a sectional view through an obstructed artery and an adjacent vein, wherein a penetration tract or blood flow channel has been formed between the artery and the vein and a polymer stent has been positioned within the penetration tract of blood flow channel.

Stents such as those shown in FIG. 4 and 4a may be necessary to control dimensions of the tissue tract 36 from expanding under pressure, or closing as a result of restenosis. Another method of maintaining the dimensions of tissue track 36 permanently or temporarily during the healing and remodeling process is shown in FIG. 7. Here a polymer stent 71 is shown covering the walls of tissue track 36. Such a polymer stent 71 may be placed either by insertion and dilation using a balloon catheter, or may created in-situ using various methods known in the art and practiced by a company by the name of FOCAL™ located in Massachusetts. Such a polymer stent 71 may permit the temporary protection from the effects of restenosis or pseudoaneurysm formation, and may dissolve after a period of time to reduce the likelihood of any long-lasting tissue reaction effects.

It may be possible that the creation of a tissue track is undesirable, due to the high likelihood that problems such as restenosis or pseudoaneurysm complicate the procedure. This problem may be overcome using methods such as those shown in FIGS. 8, 9, 9a, 9b, 9c, 22, 22a and 23.

Figure 8:
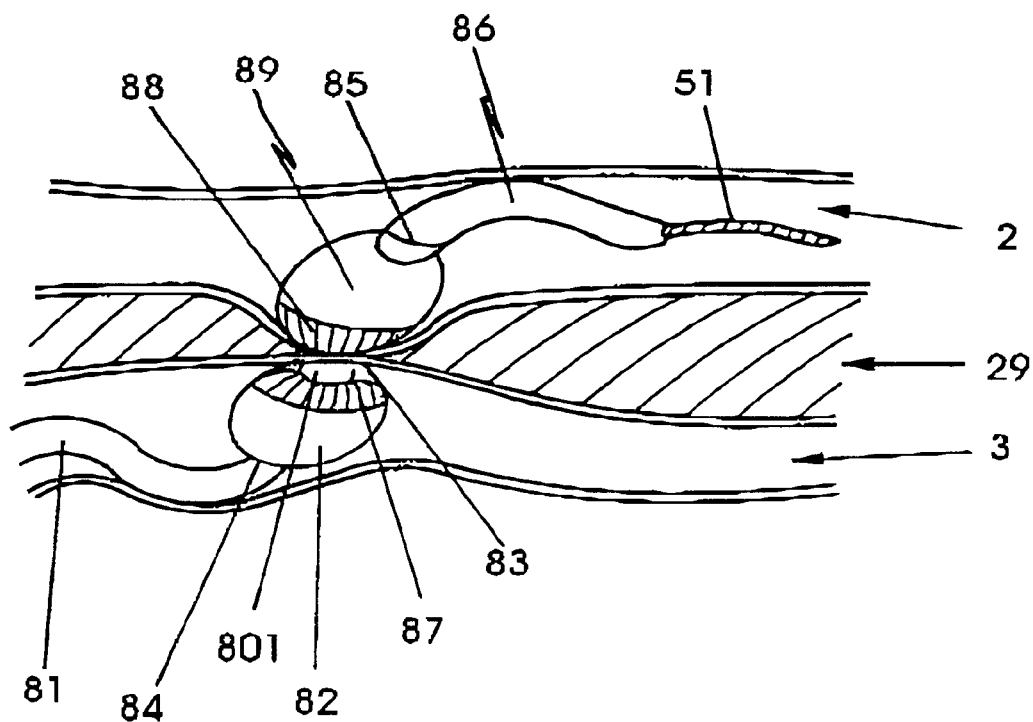
FIG. 8 is a sectional view through an obstructed artery and an adjacent vein, wherein a blood flow passageway has been formed between the artery and the vein and a welding catheter system has been inserted through the blood flow passageway and is being used to caused local tissue fusion in accordance with one embodiment of the present invention.

In FIG. 8, a welding catheter system is used which consists of proximal welding catheter 81 and distal welding catheter 86. After the tissue track is created through interstitial space 29 between cardiac vein 3 and coronary artery 2, guidewire 51 is inserted. Distal welding catheter 86 is then advanced over guidewire 51 and distal approximation balloon 89 is inflated. Subsequently, proximal welding catheter 81 may be advanced over the distal welding catheter 86. At that point, proximal approximation balloon 82 may be inflated, and the two balloons may be pulled into position, opposing the edges of the opening in the coronary artery 2 and cardiac vein 3. The approximation balloons and welding catheters may be equipped with one or more of the following components: intraweld electrodes 83, contralateral welding surfaces 87 and 88, return electrodes 85 and 84 and a thermocouple 801. In this configuration, bipolar RF energy may be used to weld the two vessel openings together without the need for additional mechanical attachment devices. Energy will be delivered either between the contralateral welding surfaces 87 and 88 or between the intraweld electrodes 83 and the return electrodes 85 and 84. In either case, the temperature of the local tissue in and around the approximated two openings is elevated to a desired temperature measured by thermocouple 801. This temperature is maintained for a certain amount of time during which time the tissue is fused. After fusion, the power is turned off, the balloons are deflated, and the apparatus is removed, leaving the two openings fused around their perimeter.

Figure 9A:
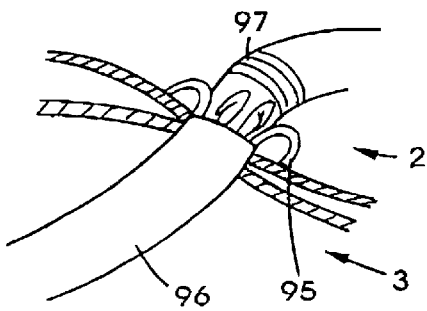
Figure 9B:
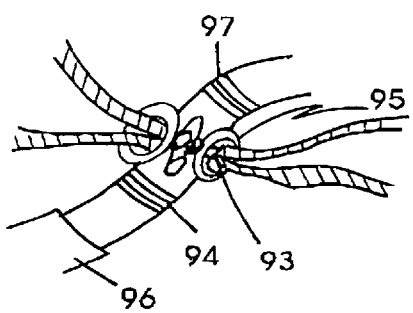
Figure 9C:
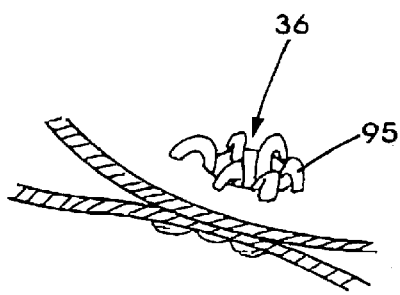

In FIG. 9 a mechanical stapling method is described to attach the two vascular openings. Stapling catheter 91 has outer sheath 96, optional heating coils 94 and 97, staples 95, and micromachine staple holders 93. Stapling catheter 91 is advanced through tissue track 36 until the device is well into the coronary artery 2. The outer diameter of the outer sheath 96 is sized to slightly dilate the tissue track 36 between the two vessels. Outer sheath 96 is pulled back until the full upper halves of staples 95 are exposed. This point of pull back is controlled at the proximal end of the catheter. The staples 95 are composed of either a spring-like material such as stainless steel, or super elastic alloy such that they spring into a curved position as seen in FIG. 9a. This effect may also be accomplished using shape memory materials such as nitinol and adding heat through coil 97. Once staples' 95 upper halves have achieved their curved state, the stapling catheter 91 can be withdrawn, as shown in FIG. 9B, allowing the tips of the staples 95 to seat into the circumference of the opening in the coronary artery 2. Now the outer sheath 96 can be fully withdrawn (as shown in FIG. 9B), permitting the lower halves of the staples 95 to seat into the inner aspect of the circumference around the opening of the cardiac vein. Again this effect can be created either passively upon release of the sheath, or actively using heat from heating coil 94. While the passive approach is more simplified, the active approach allows for the reversal of the device using an injection of cold saline. This may be desirable in cases where the seating of the staples 95 was not accomplished correctly. Finally, once the staples' placement is assured, they may be released by the micromachine staple holders 93 resulting in the configuration shown in FIG. 9C, wherein staples 95 cause the tissue 36 to be maintained in an open condition. Those skilled in the art will recognize that other than utilizing micromachines, there may be several methods of staple release, including thermal material methods such as solder melting, thermal degradation of a retaining polymer or biomaterial, as well as mechanical methods such as the removal of a retaining wire, balloon expansion of a weak retaining material, or an unlocking motion of the stapling catheter 91 with respect to the staples 95 that could only be accomplished after the staples have been fixed in place.

FIG. 22 shows another embodiment for holding together the two openings in both vessels. This embodiment utilized a distal guide catheter 2205 which is inserted over a guide wire 2206. An upper clip 2204 is held to the distal guide catheter 2205 by a collapsible retaining unit 2207 located near the upper clip 2204. This assembly is advanced through tissue track 36 until it is completely through. In this case, the collapsible retaining unit 2207 helps to dilate the tissue track 36 since the upper clip 2204 is dimensioned to be slightly larger than the diameter of tissue track 36. A proximal guide catheter 2201 with a lower clip 2202 at its tip are advanced over the distal guide catheter 2201 towards tissue track 36. The two clips 2204 and 2202 are then pulled toward each other until tines 2208 of upper clip 2204 penetrate and lock into the receiving holes 2209 located in the lower clip 2202. Upon successful locking, the collapsible retaining unit 2207 is collapsed and both proximal and distal catheters are withdrawn leaving the clips behind as seen in FIG. 22a. The collapsible retaining unit may, for example, be a balloon, struts composed of shape memory material, or wire pins controlled at the proximal end of the catheter.

Figure 23:
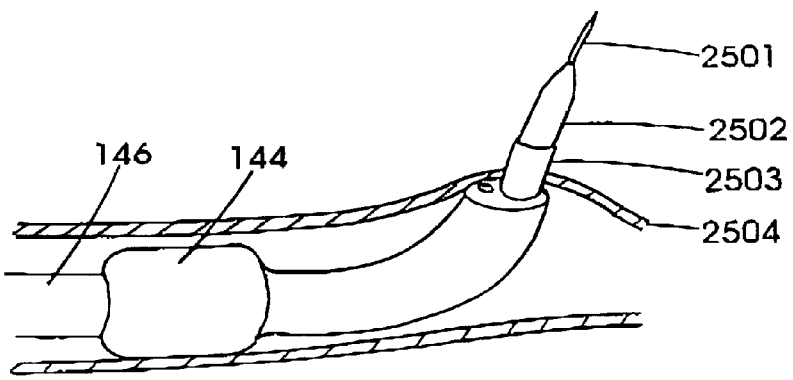
FIG. 23 is a partial sectional view of a blood vessel wherein a penetration catheter device of this invention is being used to penetrate outwardly through the wall of the blood vessel and a dilator, sheath and guidewire are being advanced through the tissue penetrator.

A further welding device in accordance with an embodiment of the present invention is detailed in FIG. 23. Here a very similar scheme to that found in FIG. 8 is employed with the exception that energy is released from a central emitter core 2301 into the opposed openings of vessels 2 and 3. In this case, after the two openings are opposed, by balloons 89 and 81, a central emitter core is advanced into the center of the catheter assembly 81 and 86 to a position directly at the midpoint of tissue track 36. Energy is emitted by this central emitter core to produce enough temperature in the local tissues surrounding the device to permit fusion. This energy and the emitter may be of the form of a 360 degree laterally firing laser fiber, microwave or other electromagnetic antennae, or locally mounted ultrasound producing piezoelectric crystal or laser emitter. Thermocouple 801 may also be helpful to define and control the welding process.

FIG. 12 depicts the final result after the coronary bypass procedure is complete. Normal coronary flow 34 is bypassed around stenosis 201 through tissue track 1202 into cardiac vein 3 and back into coronary artery 2 through tissue track 1203. Here a generic embolization device 1201 is shown blocking the upstream and downstream cardiac vein 3 in addition to a tributary vein 1204. In the case where simply cardiac venous arterialization is desired, only the proximal embolization and attachment would be required.

Figure 13:
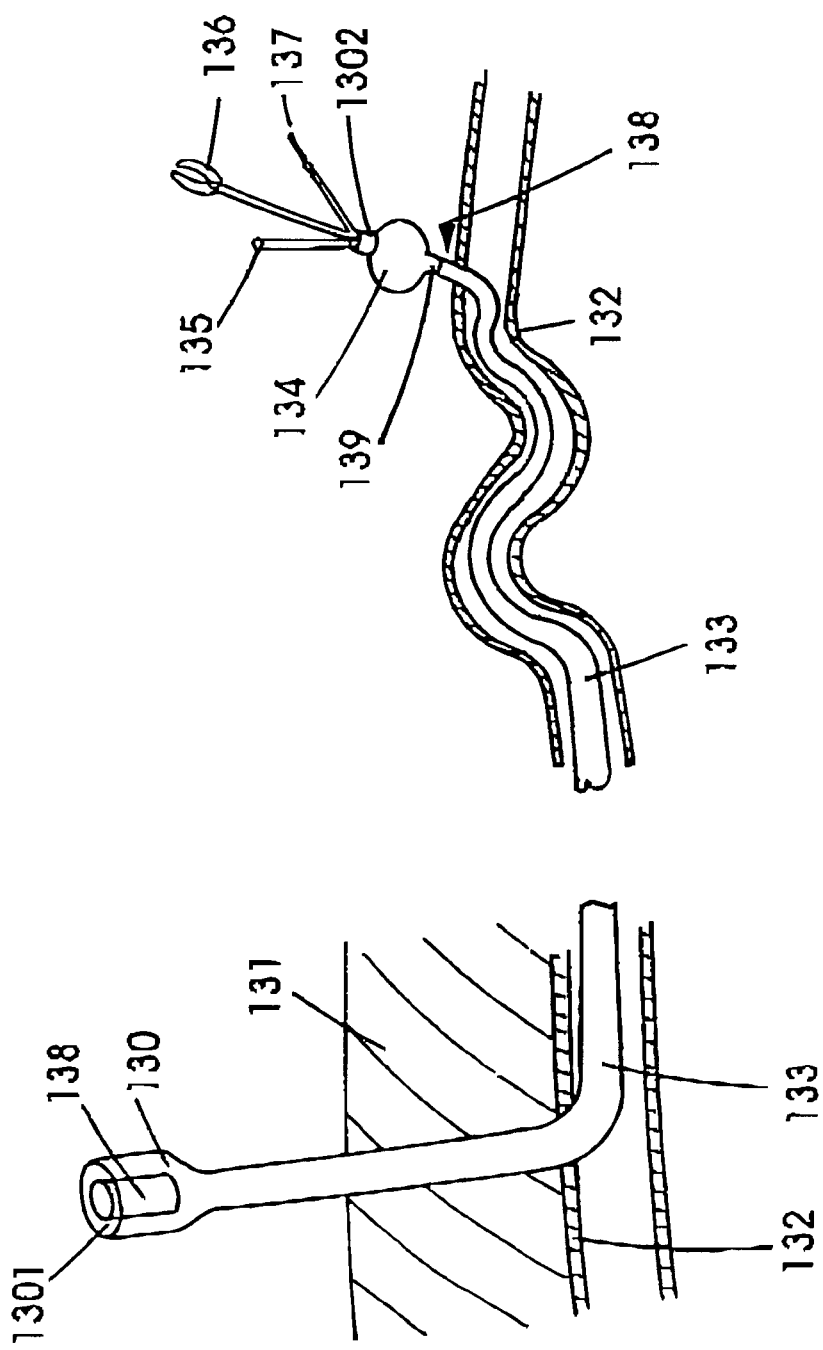
FIG. 13 is a broken, sectional view of a blood vessel being used in the performance of transvascular interstitial surgery TVIS procedure in accordnace with one aspect of the present invention.

FIG. 13 depicts a generalized TVIS access port 1301. The TVIS port has a housing 130 and an entry port 138 which permits the introduction of various instruments. The entry port 138 may also have the ability to maintain pressure or hemostasis within the catheter alone or when instruments are inserted through it. Catheter 133 has a proximal portion which forms the housing 130 and a distal portion which forms the tip 1302. The TVIS access port 1301 may also be provided with an imageable marker 139 and a stabilizing balloon 134 located at its distal portion. After the TVIS guide catheter 5 shown in FIG. 5 obtains interstitial access and leaves behind a guidewire, the distal tip of the TVIS access port 1301 is placed percutaneously over the guidewire and advanced to the interstitial location 138. Upon identification of the marker 139 outside the vessel 132, the balloon 134 is inflated. Those skilled in the art should recognize that stabilization means at the tip may also include locking wires, expandable cages, and expandable stent-like frames. Once the TVIS access port is fixed in location, numerous other devices may be inserted for effecting a medical or therapeutic intervention. These include endoscopes 135, surgical tools 136 such as needles, cannula, catheter scissors, graspers, or biopsy devices, and energy delivery devices 137 such as laser fibers, bipolar and monopolar RF wires, microwave antennae, radiation delivery devices, and thermal delivery devices. Once one or more TVIS access ports 1301 are placed, various surgical procedures may be conducted completely through the vascular system on tissues in the periphery.

Figure 14:
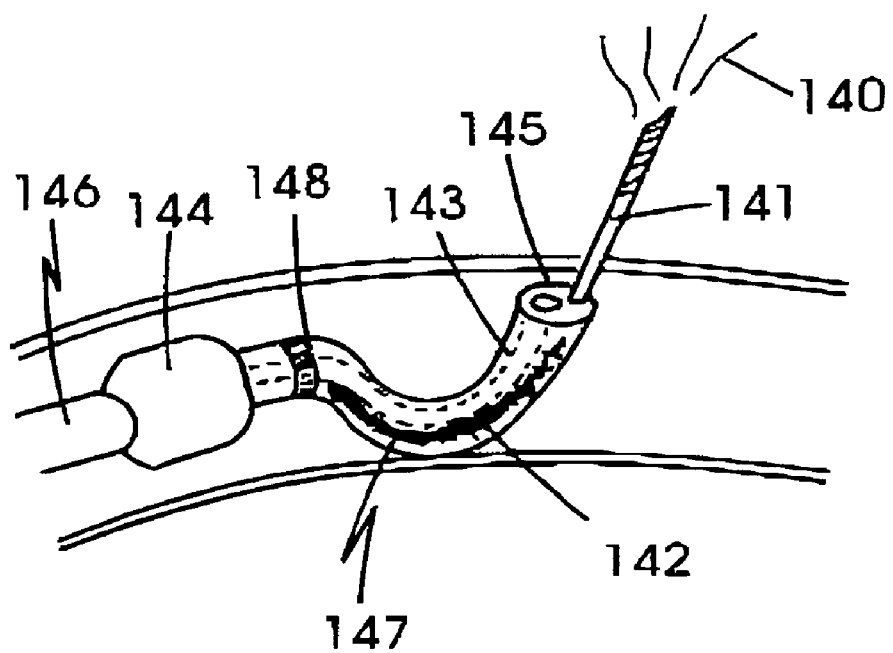
FIG. 14 is a partial sectional view of a blood vessel having a deflectable-tipped penetration catheter device of the present invention being used to puncture outwardly through the wall of the blood vessel.

FIG. 14 shows another embodiment of a TVIS guide catheter 146 in accordance with the present invention. Here the TVIS guide catheter 146 is shown having an actively deflectable distal tip 145. In this case, the distal tip 145 is deflected by a shape memory material 142 embedded in the distal tip 145 of the device. When this material is heated by heating coil 147, the material rapidly bends into a desired configuration. A working channel 143 is provided for the advancement of the desired TVIS device. Here a needle 141 is shown infusing a drug 140 into the perivascular tissue. As discussed previously, the TVIS guide catheter 146 may also include a balloon 144 for stabilization within the vessel, and a passive imaging marker 148.

Figure 15:
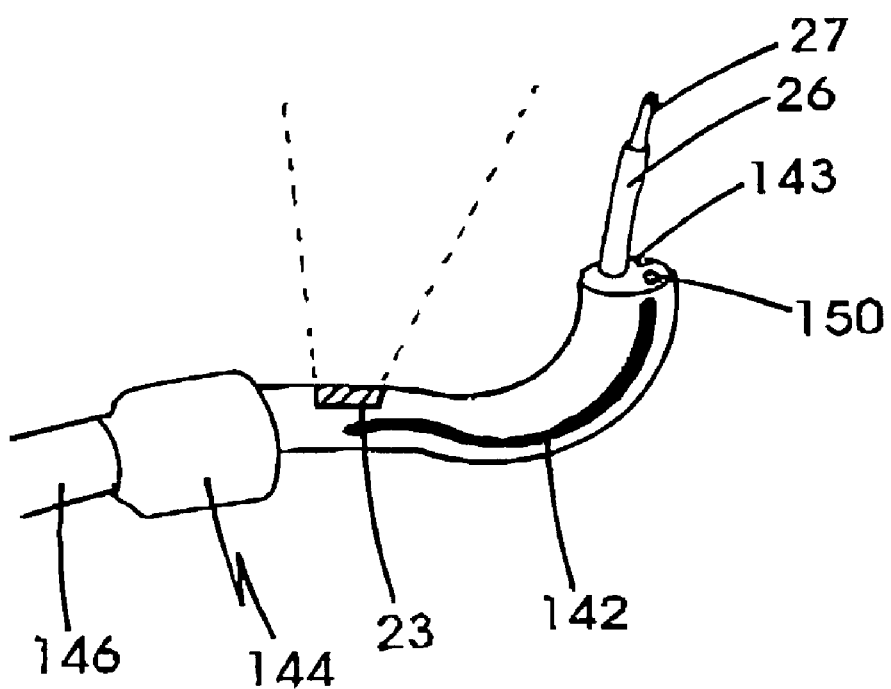
FIG. 15 is a partial perspective view of another deflectable-tipped penetration catheter device of the present invention incorporating an optional active imaging apparatus and an optional flush channel.

FIG. 15 depicts the same TVIS catheter 146 with the additional component of an active imaging device 23 as described previously. Also in FIG. 16, the TVIS probe 27 and TVIS sheath 26 are shown exiting the working channel 143 at the distal tip 145. Further, a flush channel 150 is also shown.

Figure 17:
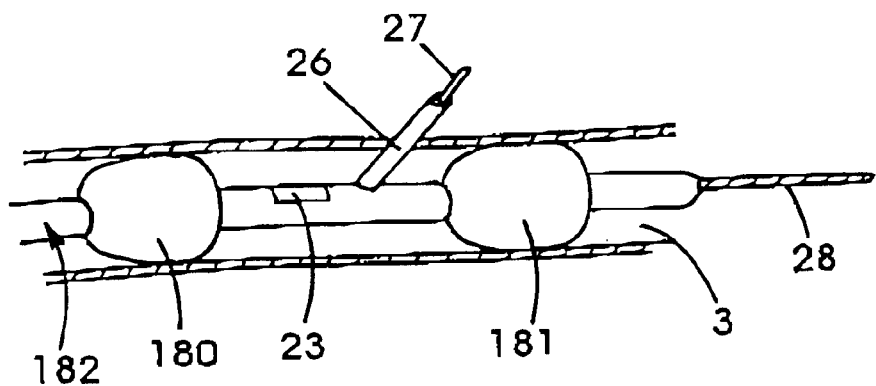
FIG. 17 is a partial sectional view of a blood vessel having a dual balloon penetration catheter device of the present invention position within the lumen of the blood vessel and being used to penetrate outwardly through the wall of the blood vessel.

FIG. 17 depicts another method of creating an accurately sized tissue track 36 in accordance with an embodiment of the present invention. A retrograde tissue cutter catheter assembly 173 is advanced over guidewire 51 through tissue track 36. The retrograde tissue cutter assembly 173 has a cylindrical blade 171 attached to a dilating tip 170. The tip 170 is advanced through the tissue track 36 until the blade 171 is beyond the opening within artery 2. Once that position is found, a much larger base catheter 172 is advanced against the proximal opening within vein 3. The blade 171 and tip 170 are then pulled back against the edges of tissue track 36, capturing tissue within the cylindrical blade 171 as it is pressed against the base catheter 172. After the assembly 173 is removed, the resulting tissue track 36 is the size of the outer diameter of the cylindrical blade 171.

Figure 18A:
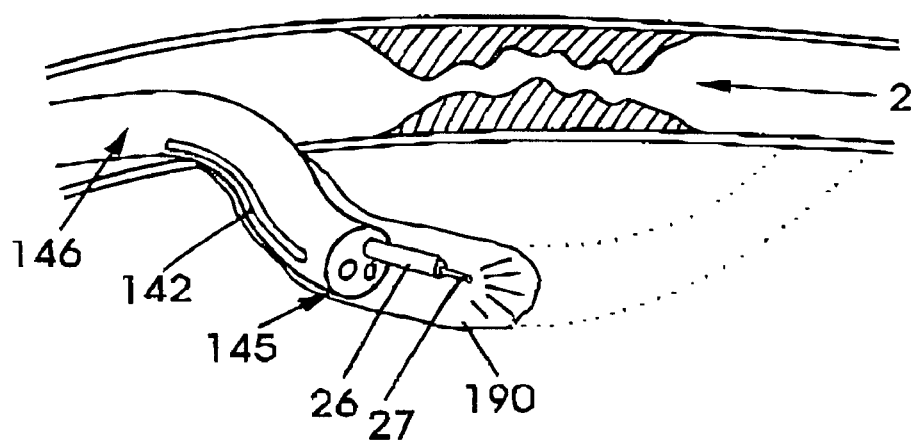
FIG. 18a is a partial sectional view of an obstructed artery wherein a catheter device of the present invention has been inserted and is being used to tunnel around the obstruction in accordance with one type of transluminal bypass procedure of the present invention.
Figure 18B:
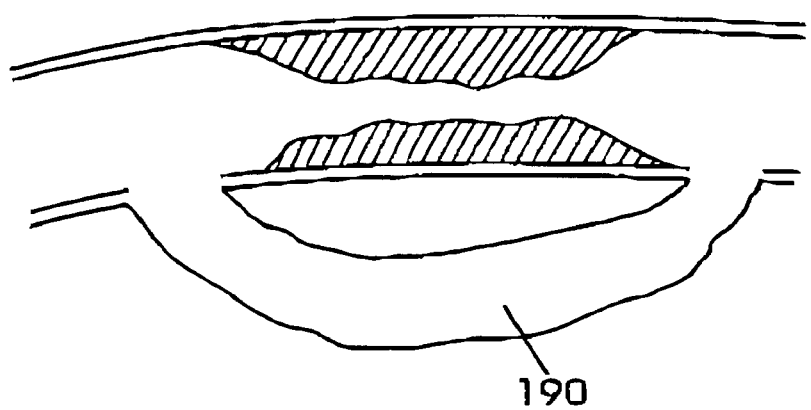
FIG. 18b is a partial sectional view of the obstructed artery of FIG. 18 after the transluminal bypass procedure has been completed.

FIG. 18 depicts a TVIS guide catheter 182 in accordance with an embodiment of the present invention where a distal balloon 181 and a proximal balloon 180 isolate a section of the artery which is to be penetrated. This may be useful when using the TVIS guide catheter 182 in a high pressure vessel such as an artery. Such a catheter 182 may be used in a manner generally similar to the catheter 5 in FIG. 2.

Figure 19:
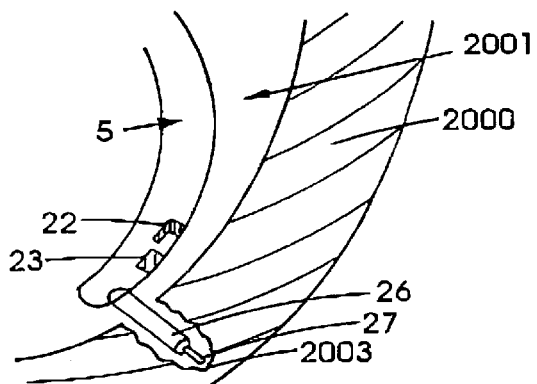
FIG. 19 is a partial sectional view of a coronary blood vessel wherein one embodiment of a penetration catheter of the present invention has been inserted and is being used to perform a transcoronary transmyocardial revascularization procedure in accordance with the present invention.
Figure 19A:
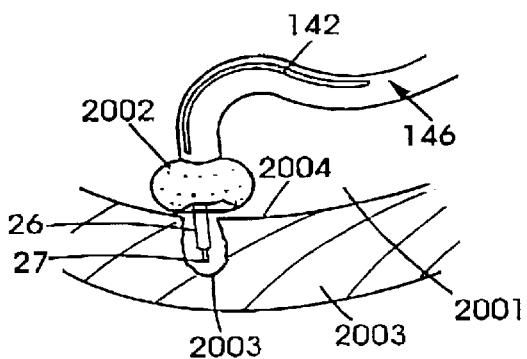
FIG. 19a is a partial view of a coronary blood vessel wherein a deflectable-tipped embodiment of a penetration catheter of the present invention has been inserted and is being used to perform a transcoronary transmyocardial revascularization procedure in accordance with the present invention.
Figure 19B:
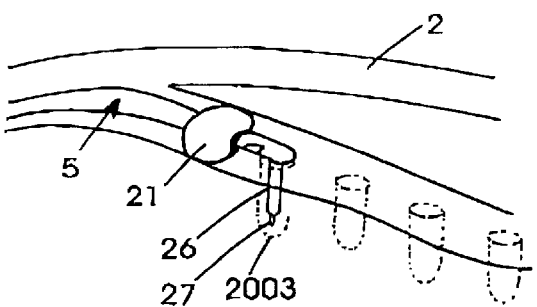
FIG. 19b is a partial sectional view of a coronary blood vessel wherein one embodiment of a penetration catheter of the present invention has been inserted and is being used to form a series of transmyocardial revascularization channels in accordance with the present invention.

Another alternative method in accordance with an embodiment of the present invention for bypassing a section of a vessel is depicted in FIGS. 19A and 19B. FIG. 19A depicts a TVIS guide catheter 146, such as described in FIGS. 14 and 15, but here having a distal tip 145 with an actively controlled shape memory material 142. Here the TVIS guide catheter 146 itself is shown tunneling through surrounding tissue utilizing probe 27 and sheath 26 to guide the way. Ultimately, the catheter 146 creates a tunnel 190 which can be used to allow flow from one point to another point in artery 2 as shown in FIG. 19B.

Figure 20:
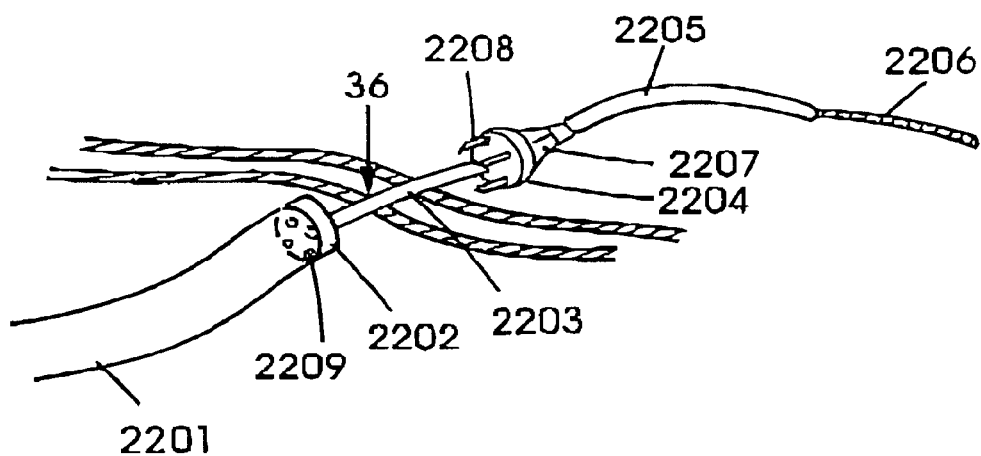
FIG. 20 is a partial sectional view of another apparatus of the present invention being deployed and implanted so as to hold together opening formed in the walls of adjacent blood vessels.
Figure 20A:
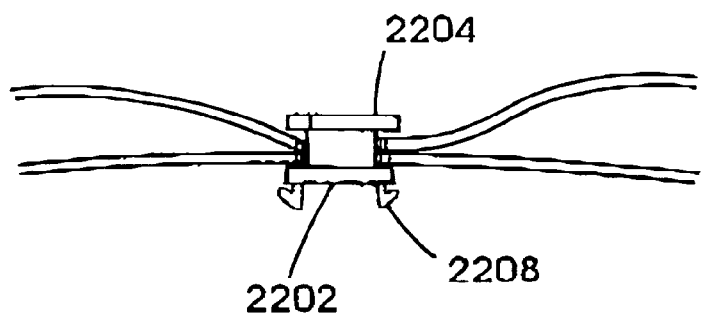
FIG. 20a is a side view of the device of FIG. 20 after the device has been fully deployed and implanted.

FIGS. 20, 20A and 20B depict the use of the device for transmyocardial revascularization in accordance with an embodiment of the present invention. FIG. 20 shows how the TVIS guide catheter 5 can be placed within the ventricle 2001 of the heart. The TVIS probe 27 is shown here creating an elongate channel 2003 through the heart muscle 2000. This channel may result in a direct communication between the ventricle and the small capillary vascular bed within the heart muscle 2000. FIG. 20A depicts how the alternative TVIS guide catheter 146 of FIG. 19A may be used to create these elongate channels 2003 within the heart. The TVIS guide catheter 146 is further modified in this case with a balloon tip 2002 for the purpose of covering the channel 2003 during vaporization; the balloon 2002 may be additionally assisted in assuring seating against the ventricle wall 2004 by providing a suction through the catheter 146 to an opening at the distal end of balloon 2002. Finally, FIG. 20B depicts TVIS guide catheter 5 creating several channels 2003 transvascularly, permitting blood flow from the vessel directly into the heart.

Figure 24A:
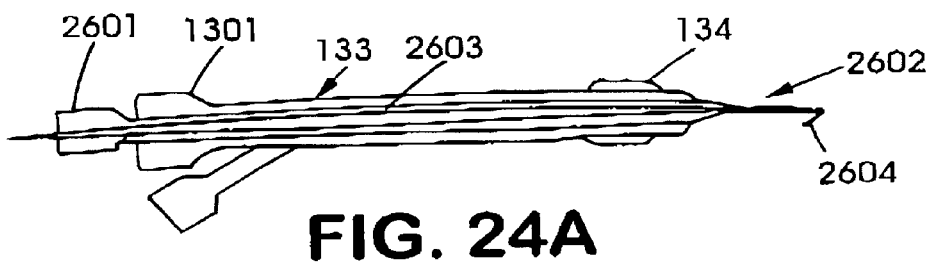
FIG. 24a is a longitudinal sectional view of a penetration catheter of the present invention in combination with a locking or anchorable guidewire.
Figure 24B:

FIG. 24A depicts a side-to-side fistula stent 2400 in accordance with an embodiment of the present invention. The stent 2400 is fashioned like a clover with the leaves at alternating heights. The two top leaves 2401 and 2403 and the two bottom leaves 2402 and 2404 are placed such that they lie on either side of the vessel edge as shown in FIG. 24B. Intervening segments 2405 which are perpendicular to the planes of the clovers 2401–2404 lie within the channel created by the TVIS devices. The device is deployed from a catheter 2407 over a guidewire 2408 as shown in FIG. 24C. The stent is wrapped around an inner sheath 2409 such that clover leaves 2401 and 2403 are distal and 2402 and 2404 are proximal. As the catheter 2407 is moved relative to sheath 2409, the two distal clovers 2401 and 2403 are released, the device is withdrawn until the lovers 2401 and 2403 come in contact with inner surface of the distal vessel. Then the catheter 2407 is moved further with respect to the sheath 2409 and the proximal clovers 2402 and 2404 are released onto the inner surface of the proximal vessel as shown in FIG. 24E.

Figure 25A:
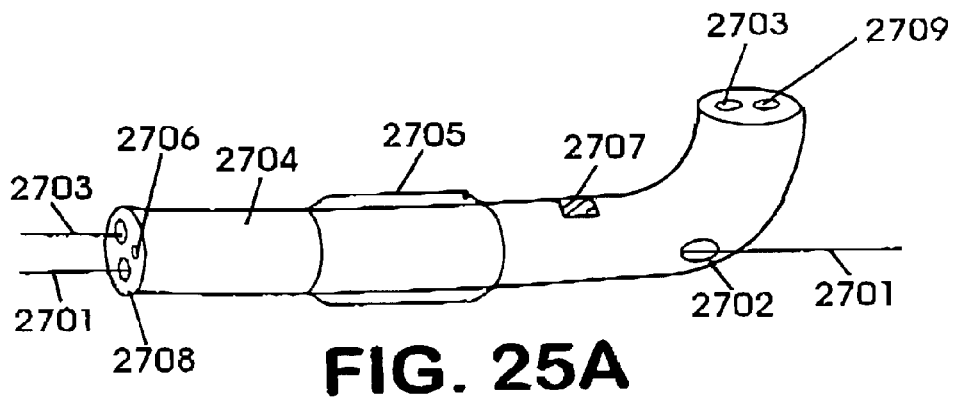
FIG. 25a is a partial perspective view of another embodiment of a penetration catheter of the present invention, having a pre-curved configuration.
Figure 25B:
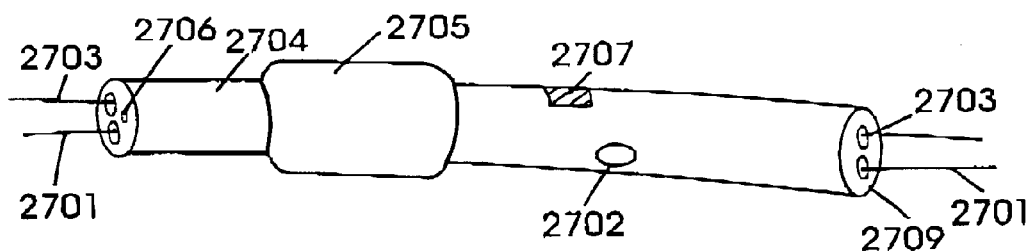
FIG. 25b is a perspective view of the pre-curved penetration catheterd ddevice of FIG. 25a being constrained to a straight configuration.

FIG. 25 depicts more detail of the various types of devices which may be advanced through the TVIS catheter 146 in accordance with an embodiment of the present invention. Here, a wire 2501 is shown having advanced over it a dilator 2502 and a sheath 2503 through the vessel wall 2504.

Figure 26:
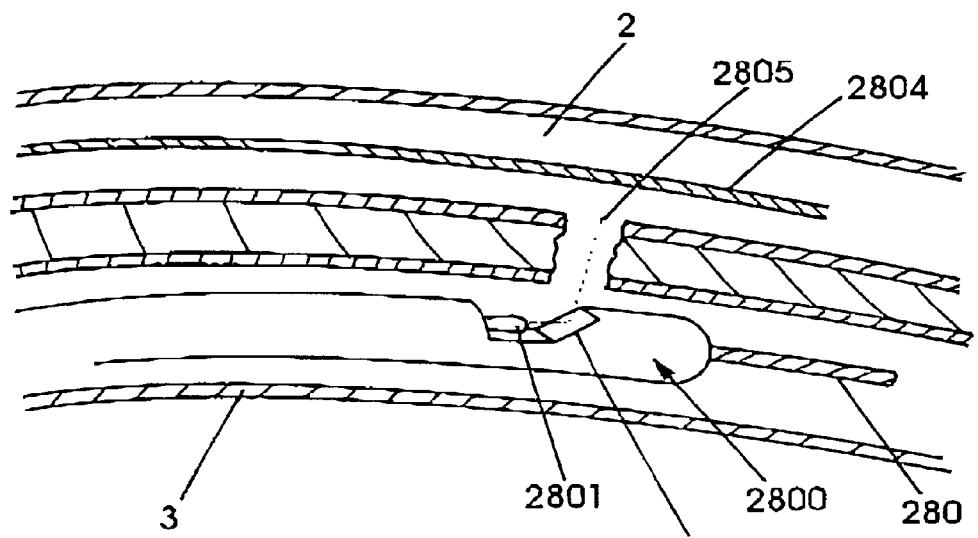
FIG. 26 is a is a partial sectional view of two blood vessel wherein an energy emitting embodiment of a penetration catheter of the present invention has been inserted and is being used to form a penetration tract or blood flow channel between the blood vessels.

Alternatively, a separate sheath such as the one shown in FIG. 13 can be advanced. FIGS. 26A and 26B show more detail on the components of such a system. Initially, the TVIS catheter is used to place a locking guidewire 2602 into the tissue. The guidewire has a very small locking tie 2604 which serves to anchor it in the tissue during device exchange. Then, over the locking guidewire 2602 the TVIS port introducer assemby shown in FIG. 26A is advanced. The assembly includes a dilator 2601 within a catheter 133. The catheter 133 is provided with a stabilization means 134 illustrated here as a balloon. After the catheter 133 is in place, and the stabilization means 134 is deployed, the dilator 2601 and the locking guidewire 2602 are removed. Depending on the situation, housing 1301 may or may not be equipped with a valve to prevent backflow into the catheter 133. Subsequently, various instruments may be inserted into the catheter 133 as described previously.

Figure 27:
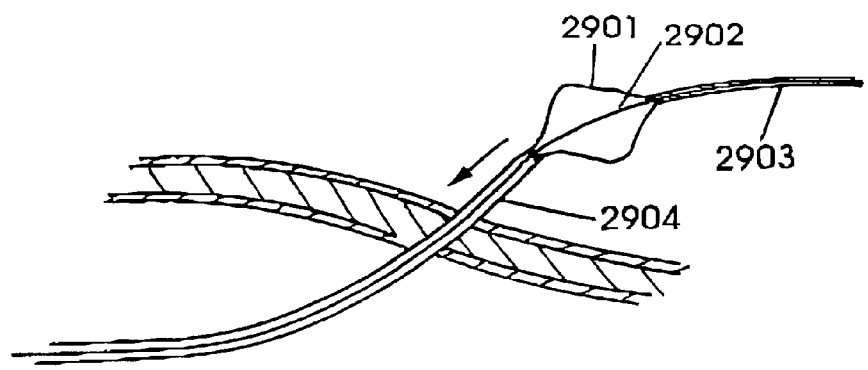
FIG. 27 is a partial sectional view of two blood vessels wherein a penetration tract has been formed between the blood vessels and a cutting-type channel sizing device has been advanced through the penetrating tract and is being used to enlarged the penetration tract to create a blood flow channel in accordance with one aspect of the present invention.

Another embodiment of the TVIS catheter in accordance with the present invention can be seen as item 2704 in FIGS. 27A and 27B. Here the TVIS catheter 2704 is made with a pre-formed curve seen in FIG. 27A. When the catheter is constrained as seen in FIG. 27B it can be held in a linear position. Guidewire 2701 can be seen exiting the guidewire lumen 2709 when the catheter 2704 is held linearly (FIG. 27B) and can exit the side hole 2702 when the catheter is allowed to regain its preformed shape (FIG. 27A). A TVIS probe 2703 is shown entering another channel and exiting the device at the tip in either position. The catheter 2704 can be used in the manner of other catheters discussed previously but has the benefit of being able to cause the tip to be curved in a desired direction.

A further embodiment of a TVIS catheter 2800 in accordance with the present invention is shown in FIG. 28. Here the two openings in the vessels are made with a vaporizing energy beam 2805 instead of a probe. This method utilizes an energy guide 2801, which beams energy at a deflecting plate 2802, which in turn sends the energy laterally into the tissue. The duration and energy level must be finely set to ensure that the opposite wall of vessel 2 is not damaged. Also shown in the diagram is the optional guidewire 2804, which may be used to block or signal the penetration of the laser energy.

FIG. 29 depicts another mechanism for widening or cutting the hole in accordance with an embodiment of the present invention. Here the device is advanced through the tissue channel over guidewire 2903, the cutting wings 2901 are expanded by moving sheath 2904 relative to central body 2902. The wings 2901 may be sharp, or the use of additional energy may be used to widen the hole as the device with withdrawn through the tissue channel.

Figure 16:
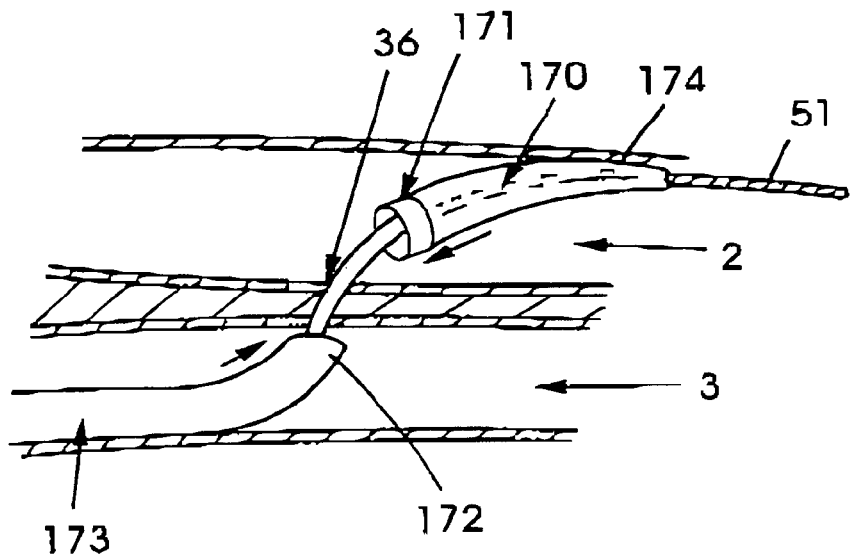
FIG. 16 is a sectional view through two adjacent blood vessels, wherein penetration tract has been formed between the blood vessels and pull back channel sizing device has been advanced through the penetration tract and is being used to enlarge the penetration tract to form a blood flow channel.
Figure 21:
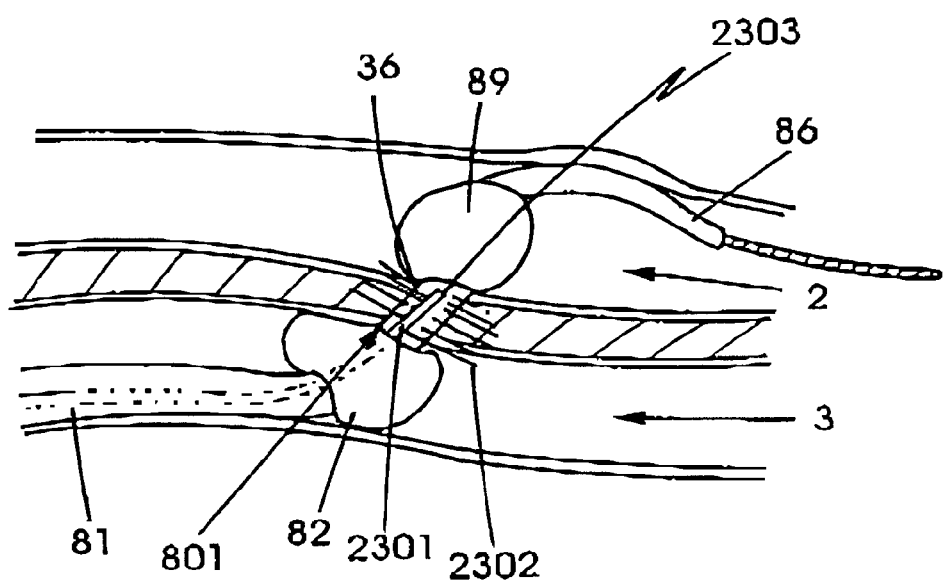
FIG. 21 is a view of a welding device.
Figure 22A:
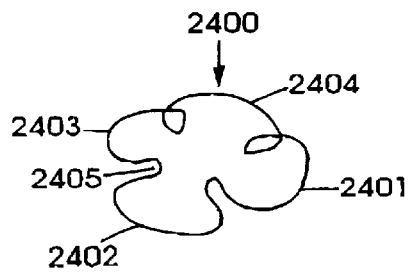
FIGS. 22a–22e are a step-by-step showing of a method for implanting another connector device of the present to hold together openings formed in the walls of adjacent blood vessels.
Figure 22B:
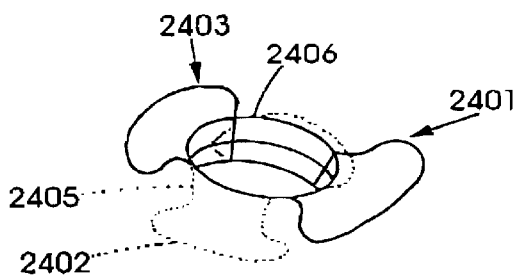
Figure 22C:
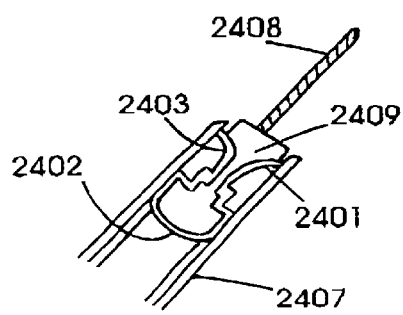
Figure 22D:
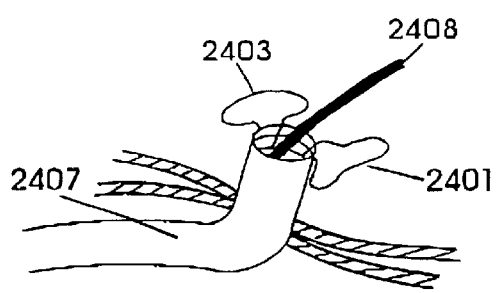
Figure 22E:
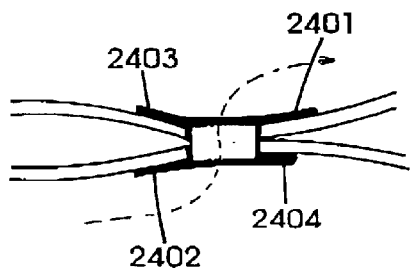

FIGS. 16 and 21 are intentionally omitted.

What is claimed is:

1. A catheter device for delivering a substance to a target site located outside of the lumen of a blood vessel;
   a catheter that is advanceable into the blood vessel lumen;
   a penetrator that is advanceable from the catheter;
   a lumen extending through the penetrator; and,
   trajectory indicating apparatus for indicating the trajectory on which the penetrator will advance relative to the location of the target site, thereby enabling an operator to place the catheter in such position and rotational orientation within the blood vessel lumen that the penetrator will advance from the catheter, out of the blood vessel lumen to the target site.

2. A catheter device according to claim 1 wherein the trajectory indicating apparatus comprises a passive marker.

3. A catheter device according to claim 1 wherein the trajectory indicating apparatus comprises an active marker.

4. A catheter device of claim 1 wherein the trajectory indicating apparatus comprises a marker that may be sensed by a magnetic apparatus.

5. A catheter device according to claim 1 wherein the trajectory indicating apparatus comprises marker that may be imaged by a radiographic imaging apparatus.

6. A catheter device according to claim 1 wherein the trajectory indicating apparatus comprises a) an imageable marker which indicates the trajectory on which the penetrator will subsequently advance and b) imaging apparatus for concurrently imaging the target site and the imageable marker.

7. A catheter device according to claim 6 wherein the imageable marker is located on or in the catheter.

8. A catheter device according to claim 7 wherein both the imageable marker and the imaging apparatus are located on or in the catheter.

9. A catheter device according to claim 7 wherein the imageable marker is located on or in the catheter and the imaging device is not located on or in the catheter.

10. A catheter device according to claim 7 wherein the imaging device is located on or in the catheter and the imageable marker is not located on or in the catheter.

11. A catheter device according to claim 1 wherein the trajectory indicating apparatus is operative to sense flow within the target location.

12. A catheter device according to claim 1 wherein the trajectory indicating apparatus comprises a transmitter and receiver.

13. A catheter device according to claim 12 wherein one of the transmitter and receiver are positionable at the target site.

14. A catheter device according to claim 1 wherein the penetrator comprises a hollow needle through which the substance may be injected.

15. A catheter device according to claim 1 wherein the penetrator comprises a curved hollow needle through which the substance may be injected.

16. A method for delivering a substance to a target site located outside the lumen of a blood vessel, said method comprising the steps of:

A. providing a catheter device which comprises i) a catheter, ii) a penetrator that is advanceable from the catheter, iii) a lumen extending through the penetrator and, iv) trajectory indicating apparatus for indicating the trajectory on which the penetrator will advance relative to the location of the target site, thereby enabling an operator to place the catheter in such position and rotational orientation within the blood vessel lumen that the penetrator will advance from the catheter, out of the blood vessel lumen to the target site.

B. positioning the catheter device within the lumen of the blood vessel;

C. using the trajectory indicating apparatus to obtain an indication of the trajectory on which the penetrator will subsequently advance from the catheter;

D. making any necessary adjustments to the position and/or rotational orientation of the catheter within the blood vessel lumen to cause the indication of the trajectory on which the penetrator will subsequently advance from the catheter to indicate that when subsequently advanced the penetrator will enter the target site;

E. advancing the penetrator from the catheter, out of the blood vessel lumen and into the target site; and, E. infusing the substance through the lumen of the penetrator and into the target site.

17. A method according to claim 16 wherein the blood vessel is a vein.

18. A method according to claim 16 wherein the blood vessel is an artery.

19. A method according to claim 16 wherein the blood vessel is a coronary vein.

20. A method according to claim 16 wherein the blood vessel is a coronary artery.

21. A method according to claim 16 wherein the substance is a drug.

* * * * *